(12) United States Patent
Kostamovaara et al.

(10) Patent No.: US 9,395,247 B2
(45) Date of Patent: Jul. 19, 2016

(54) MEASUREMENT OF RAMAN RADIATION

(71) Applicants: OULUN YLIOPISTO, Oulu (FI); TEKNOLOGIAN TUTKIMUSKESKUS VTT, VTT (FI)

(72) Inventors: Juha Kostamovaara, Oulu (FI); Jussi Tenhunen, Kiiminki (FI)

(73) Assignees: Oulun Yliopisto, Oulu (FI); Teknologian Tutkimuskeskus VTT, VTT (FI)

( * ) Notice: Subject to any disclaimer, the term of this patent is extended or adjusted under 35 U.S.C. 154(b) by 0 days.

(21) Appl. No.: 14/767,828

(22) PCT Filed: Feb. 13, 2014

(86) PCT No.: PCT/FI2014/050111
§ 371 (c)(1),
(2) Date: Aug. 13, 2015

(87) PCT Pub. No.: WO2014/125171
PCT Pub. Date: Aug. 21, 2014

(65) Prior Publication Data
US 2015/0369666 A1    Dec. 24, 2015

(30) Foreign Application Priority Data
Feb. 15, 2013  (FI) .................................. 20135144

(51) Int. Cl.
*G01J 3/44* (2006.01)
*G01J 3/28* (2006.01)
*G01N 21/65* (2006.01)

(52) U.S. Cl.
CPC ............. *G01J 3/4412* (2013.01); *G01J 3/2803* (2013.01); *G01J 3/44* (2013.01); *G01J 3/4406* (2013.01); *G01N 21/65* (2013.01)

(58) Field of Classification Search
CPC ......... G01J 3/02; G01J 3/44; H01J 37/32935; G01N 21/64; G01N 21/65; G01N 21/68; G01N 2021/656; G01N 2015/1037
USPC ............................................... 356/301, 72–73
See application file for complete search history.

(56) References Cited

U.S. PATENT DOCUMENTS

| 5,719,672 A | 2/1998 | Chien |
| 2006/0197947 A1 | 9/2006 | Wang et al. |

(Continued)

FOREIGN PATENT DOCUMENTS

| DE | 10 2010 005 723 A1 | 1/2010 |
| FR | 2 920 869 A1 | 3/2009 |

(Continued)

*Primary Examiner* — Abdullahi Nur
(74) *Attorney, Agent, or Firm* — Birch, Stewart, Kolasch & Birch, LLP (57) ABSTRACT

An apparatus comprises a semiconductor single-photon avalanche detector, and a counter. The detector performs detections of photons of optical radiation caused by an optical excitation pulse to the object. The counter measures timing of each detection made in the detector with respect to the excitation pulse causing the detected photons, and performs at least one of the following: forming a number of Raman detections, forming a number of fluorescence detections. Forming the number of the Raman detections is performed by eliminating an estimate of a number of fluorescence photons in the measurement. Forming the number of the fluorescence detections is performed by eliminating an estimate of a number of Raman photons in the measurement. The estimates are formed in a predetermined manner from the number and timing of the detections.

23 Claims, 5 Drawing Sheets

(56) References Cited

U.S. PATENT DOCUMENTS

| | | |
|---|---|---|
| 2007/0013908 A1 | 1/2007 | Lee et al. |
| 2007/0252978 A1 | 11/2007 | Van Der Voort et al. |
| 2011/0027803 A1* | 2/2011 | Moussavi ............... C08F 2/005 |
| | | 435/7.9 |
| 2011/0261354 A1 | 10/2011 | Sinfield et al. |
| 2013/0342835 A1 | 12/2013 | Blacksberg |

FOREIGN PATENT DOCUMENTS

| | | |
|---|---|---|
| WO | WO 2009/012222 A1 | 1/2009 |
| WO | WO 2009/030698 A1 | 3/2009 |
| WO | WO 2011/045469 A1 | 4/2011 |

* cited by examiner

MEASUREMENT OF RAMAN RADIATION

FIELD

The invention relates to a measurement of Raman radiation.

BACKGROUND

Raman radiation results from inelastic scattering. When monochromatic excitation radiation is directed to the object material, low-energy modes, such as vibration and rotation of molecules cause small deviations in the wavelength of the monochromatic radiation. Each deviation, in turn, is characteristic to each molecule in the material and hence a composition of the material can be identified.

The Raman radiation is notoriously difficult to measure since its intensity with respect to the excitation radiation is very low and it arrives at the detector almost simultaneously with the excitation radiation. Additionally, the excitation radiation gives rise to fluorescent radiation which is also simultaneous with the Raman radiation and whose lifetime is in nanosecond range which is longer than that of Raman radiation.

Notch filters are usually employed to block the excitation radiation away as effectively as possible without attenuating other wavelengths excessively. The Raman radiation has also been separated from the fluorescent radiation using a gating device in front of the detector. For example, an optically controlled Kerr-gate may be placed in front of a detector. In that way, only the photons detected when the gate is open can be counted which is used to suppress both the excitation radiation and the fluorescent radiation and the Raman radiation can be detected.

Instead of Kerr-gate, an image intensifier may correspondingly be placed in the front of the detector such as a CCD camera (Charge Coupled Device). The image intensifier can be switched on and off with a frequency in a megahertz range and with a gate period of several hundreds on picoseconds.

However, there are problems related to the prior art. The duty cycle of a Kerr-gate is low, which makes the measurement unpractical. The operation of the Kerr-gate also needs high-energy optical pulses which drastically limit the energy of the optical pulses directed to the measured object from the same optical source. Correspondingly, the image intensifier has a problem due to a difficult and contradictious requirement of forming short pulses with well over 1000V. In general measurement systems which have gating are slow, complicated, difficult or impossible to adjust, expensive and large such that they can only be used in laboratory.

Hence, there is a need for a better solution to measure Raman radiation.

BRIEF DESCRIPTION

According to an aspect of the present invention, there is provided an apparatus as specified in claim 1.

According to another aspect of the present invention, there is provided a method as specified in claim 18.

According to another aspect of the present invention, there is provided an apparatus as specified in claim 22.

The invention provides advantages. No gating devices are needed in or in front of the detector. Each of the detections is time-labeled individually and hence the counting of detections is easy and accurate which enables a reliable way to estimate strength of fluorescence, Raman scattering or both.

LIST OF DRAWINGS

Embodiments of the present invention are described below, by way of example only, with reference to the accompanying drawings, in which.

DESCRIPTION OF EMBODIMENTS

The following embodiments are exemplary. Single features of different embodiments may be combined to provide other embodiments.

Figure 1:
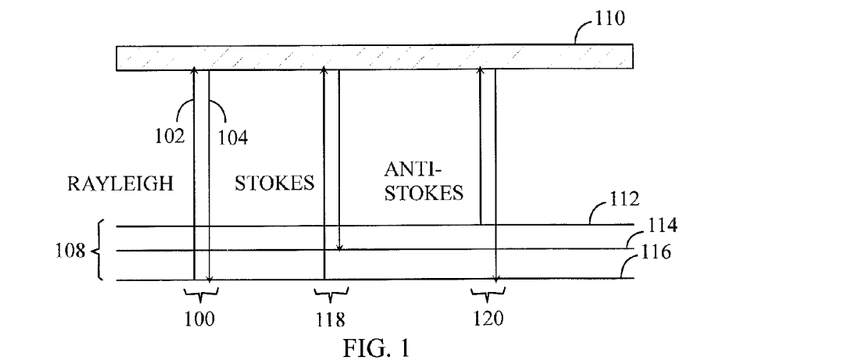
FIG. 1 illustrates an example of interaction of optical radiation and matter.

FIG. 1 shows a simplified principle of interaction between optical radiation and matter. Optical radiation can be considered to occupy a band from about 50 nm to about 500 μm. In Rayleigh scattering 100, absorption 102 of a photon has the same energy as emission 104 of a photon. In absorption of a photon, a total molecular energy jumps from a normal energy level 108 to an excited energy level 110. When the total molecular energy returns back from the excited level 110 to the normal level 108, a Rayleigh photon is emitted. The changes in the total molecular energy can be considered as shifts of electrons between different energy states in the molecule.

However, the normal energy level 108 may have several sub-levels 112, 114, 116 due to vibrational and/or rotational modes, for example, and in Raman scattering the total molecular energy may return from an excited level 110 which may be real or virtual to a different sub-level 112, 114, 116 than the sub-level it shifted from. When absorption 102 has a higher energy than emission 104, the emitted Raman radiation is based on Stokes scattering 118, and when the energies of absorption and emission are vice versa, the emitted Raman radiation is based on anti-Stokes scattering 120.

In the case of fluorescence, the interaction can basically be considered rather similar to the Rayleigh and Raman scattering. The wavelengths of fluorescence and Raman scattering are overlapping in general, and that is why they are difficult to separate. However, the emitted fluorescence radiation may have a slightly longer wavelength than the optical radiation absorbed by the matter and that is why the wavelength and thus the energy of fluorescence radiation may at least partly differ from those of Raman radiation. Hence, optical filters may sometimes be used to limit either Raman radiation or fluorescence in the detection.

Figure 2A:
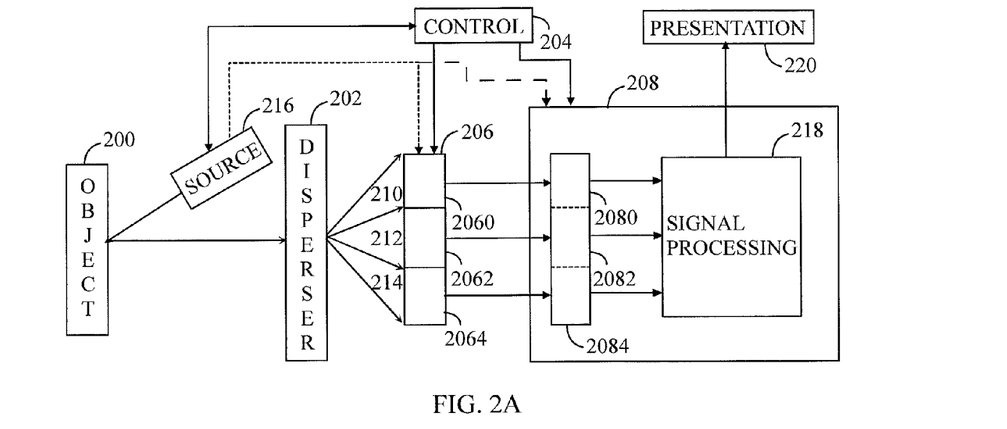
FIG. 2A presents an example of an apparatus with a disperser for measuring inelastic radiation.

FIG. 2A shows a measurement configuration of Raman radiation. However, it may correspondingly be used to measure fluorescence by suppressing Raman radiation. A source 216 of optical radiation, which may be a part of apparatus for measuring Raman radiation, may direct excitation pulses of optical radiation to an object 200. The source 216 may be a laser which is capable of outputting short pulses at a desired wavelength. The laser may be a Nd:YAG (Neodymium doped Yttrium Aluminium Garnet) laser operating at 1064 nm wavelength, for example. The second harmonics (532 nm) or higher harmonics of the Nd:YAG laser could also be used. The optical pulses may have a duration about 1 ms to 1 ps, for example. The repetition rate of the optical pulses may be about 0.1 Hz to 1 GHz for example. However, the solution is not restricted to these pulse durations and repetition rates. The source 216 may comprise one or more suitable optical components for forming the beam to diverge, converge or collimate, for example. A converging beam may be focused to the object 200. The object 200 may comprise at least one substance which may be measured on the basis of its/their unique Raman spectrum, for example. The object 200 may comprise gas, liquid or solid. A solid material may have one or more particles. The solid material may be powder.

The apparatus for measuring Raman radiation from an object 200 comprises a detector 206 and a counter 208. The detector 206 may have a plurality of semiconductor single-photon avalanche diode (SPAD) elements 2060, 2062, 2064. The counter 208 may be a TDC-circuit performing a time-to-digital conversion for timing each occurrence of a photon. The apparatus may also comprise a disperser 202 which may comprise a prism, a diffraction grating or a spectrograph. The disperser 202 may disperse different bands 210 to 214 of wavelengths i.e. photons of different energies in different directions such that photons of different energies propagate to different detector elements 2060 to 2064. The disperser 202 may be used to provide a spectrum of fluorescence and/or Raman radiation, and the disperser 202 may separate fluorescence and Raman radiation from each other at least partly. The detector array 206 detects photons of optical radiation formed in an interaction between an optical excitation pulse of the source 216 and the object 200. Photons of different energies i.e. wavelengths may be detected simultaneously. The detection means that each time when a photon arrives at and then interacts with a detector element 2060 to 2064, the photon triggers the detector element 2060 to 2064 to output an electric signal as a response.

The counter 208 receives the electric signals from the detector elements 2060 to 2064 and measures individually timing of each detection made in the detector array 206 with respect to the excitation pulse the timing of which is directly or indirectly conveyed to the counter 208. The counter 208 may comprise a separate counting unit 2080, 2082, 2084 for each optical band. In example of FIG. 2A, there are separate counting units 2080 to 2084 for each detector element 2060 to 2064. Instead, two or more detector elements 2060 to 2064 may be coupled with one counting unit which is possible when temporal difference between detections is long enough such that a detector element 2060 to 2064 recovers from the previous detection. In such a case, the detector elements may feed their identification data to the counting units 2080 to 2084 for defining which detector element performed the detection. The detector elements 2060 to 2064 are physically in different positions and it may be useful to distinguish which detector element at which position detected a certain photon.

The counter 208 may comprise a signal processing unit 218 which may comprise a processor, one or more memory and at least one suitable computer program for counting, processing the counts and storing data related to Raman radiation and fluorescence.

Figure 2B:
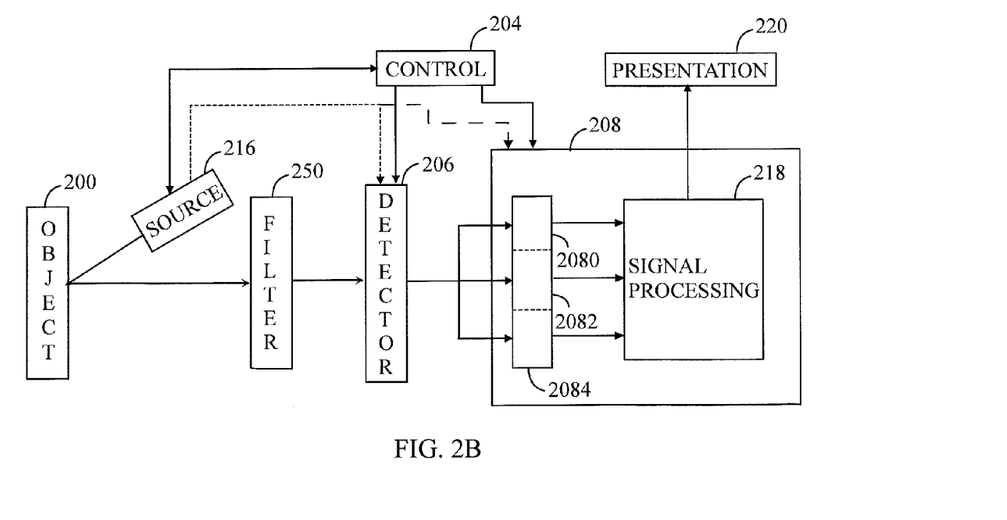
FIG. 2B presents an example of an apparatus with a filter for measuring inelastic radiation.
Figure 5:
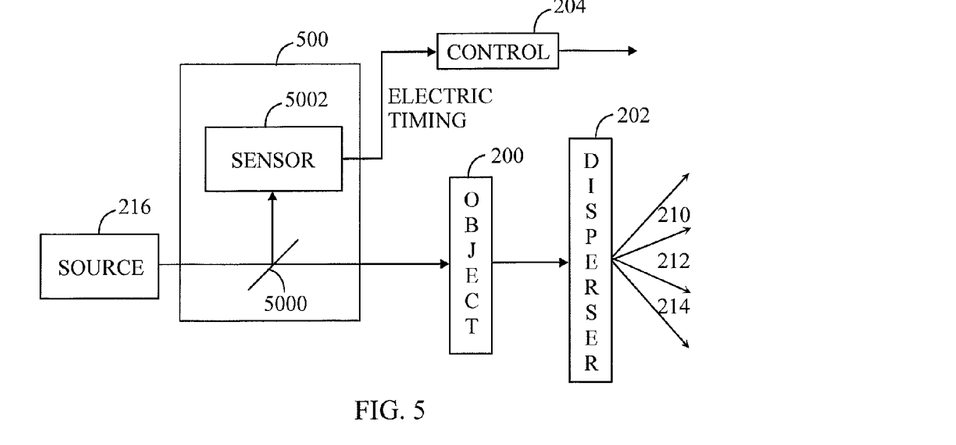
FIG. 5 illustrates an example of optical basis for a timing mark.
Figure 6:
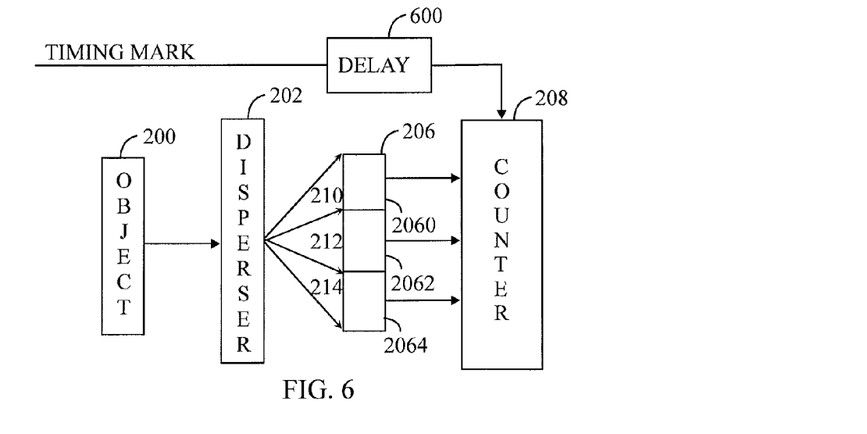
FIG. 6 illustrates an example of a delay circuit.

In an embodiment shown in FIG. 2B, a disperser 202 may be replaced by an optical filter 250 which directs different optical bands to the detector 206 at different moments of time. That is, instead of performing detections of different optical bands parallel from one excitation pulse they may be detected serially from different excitation pulses. Optical radiation from the object 200 may propagate through the filter 250 or the filter 250 may reflect the optical radiation to the detector 206. The filter 250 may have a plurality of filter elements each of which has a different pass band, and at different moments of detection a different filter element may be moved to the path of the optical radiation from the object 200 to the detector 206. Instead of mechanical movements of filter elements, the pass band of the filter 250 material may be controlled electrically. In this embodiment of serial detections, the detector 206 may have only one semiconductor single-photon diode. In example of FIG. 2B, there are separate counting units 2080 to 2084 for each detected optical band. The separate counting units 2080 to 2084 may comprise memories or parts of a memory storing the number of detections in optical bands unique to them. Although the disperser 202 is shown in FIGS. 5 and 6, the filter 250 may also be used in the examples presented with FIGS. 5 and 6.

Figure 3:
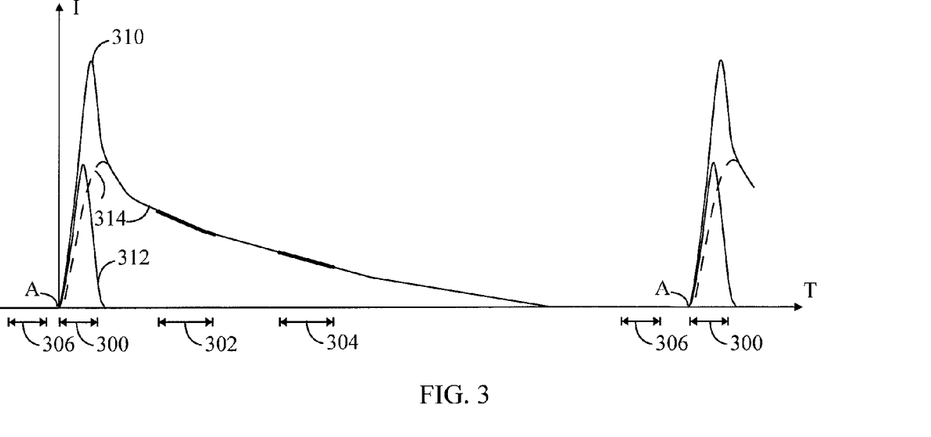
FIG. 3 illustrates an example of using different optical radiations generated by the excitation pulses, and time windows used in the measurement.

FIG. 3 illustrates intensity I of Raman radiation 312, fluorescence 314 and their combined intensity 310 as a function of time T. The intensity may also be understood to be a number of single photon detections at each moment by the detector 206. The counter 208 measures timing of each single photon detection made in the detector 206 with respect to the excitation pulse which causes the detected photons. The counter 208 forms a number of Raman detections, a number of fluorescence detections or both a number of Raman detections and a number of fluorescence detections. Forming the number of the Raman detections is performed by eliminating an estimate of a number of fluorescence photons in the measurement, the estimate being formed in a predetermined manner from the number and timing of the detections. Forming the number of the fluorescence detections is performed by eliminating an estimate of a number of Raman photons in the measurement, the estimate being formed in a predetermined manner from the number and timing of the detections. The estimate of fluorescence photons in the measurement and the estimate of a number of Raman photons in the measurement may be based on a theory of fluorescence an Raman scattering, earlier measurements or a simulation in association with the knowledge of measurement configuration and the measured material(s). In this manner, the strength of fluorescence and/or Raman scattering may be estimated in an accurate and a reliable manner.

FIG. 3 also illustrates an embodiment having different time windows 300, 302, 304, 306 which may be used in post-processing during counting the detections. The predetermined time windows 300 to 306 of post-processing may be used in a similar manner in conjunction with different excitation pulses such that both the excitation pulse and the time windows 300 to 306 have every time the same relation to each other. Hence, when a measurement sequence comprising counting of detections is completed for one excitation pulse, a similar measurement sequence may be made for the next excitation pulse. The counter 208 may count a number of detections in at least two different predetermined time windows 300 to 304 on the basis of the timing of the detections with respect to a corresponding excitation pulse.

One of the predetermined time windows may be called a Raman window 300 the beginning moment of which is about at an arrival A of the optical radiation from the interaction between the optical excitation pulse and the object to the array 206. The moment of the arrival A depends on the moment of the generation of an excitation pulse and the distance between detector array 206 and the object 200 and the distance of the source 216 and the object 200. Although it is not exactly correct, the arrival A may, for simplicity, be imagined to be the moment of generation of the excitation pulse.

The temporal length of the Raman window 300 may be determined by experiments. The duration of the Raman window 300 from the beginning to the end may be about 10 ps to 500 ps, for instance. One or more separate predetermined time windows may be called fluorescence windows 302, 304 the beginning moment of which is after a beginning of the Raman window 300. The Raman window 300 may also end before the beginning of the first fluorescent window 302, 304. It is assumed the most photons detected in the fluorescence window 302, 304 are generated by fluorescence. The duration of the fluorescence window 302, 304 from the beginning to the end may be about 1 ns to 10 ns, for instance. The durations of the time windows 300, to 304 are not limited to the values expressed in this chapter. The length of the time windows 300 to 306 can also be adjusted after the detections have been made. By selecting the lengths of the time windows 300 to 306 suitably case by case, the measurement result may be made more accurate. Note that electrical gating of the detecting and/or counting circuits has the fastest rise and fall times in the order of tens of picoseconds which limits the proper detections of photons. The timing of the detections in the time windows 300 to 306 has inaccuracy in the order of tens of picoseconds or less which makes it precise and the results reliable.

The fluorescence curve 314 has a known form which can mathematically be expressed as a time dependent function $f_f(T)$. The signal processing unit 218 may store the data or it may otherwise be available to it from a separate data base. If the fluorescence level is measured in at least one fluorescence window 302, 304, the whole fluorescence curve 314 can be estimated by setting one or more coefficients such that the value(s) of the function $f_f(T)$ with the temporal argument(s) of window(s) 302, 304 matches with the measured value(s). For example, the dashed line in the Raman window 300 can be estimated on the basis of either or both thickened lines in fluorescence windows 302, 304. Then the Raman curve 312 can be formed by subtracting the dashed line from the combined line 310 in the Raman window 300.

The counter 208 forms a number of Raman detections by eliminating an estimate of a number of detections of fluorescence photons in the Raman window 300 on the basis of a number of detections in the at least one fluorescence window 302, 304. Alternatively or additionally, the counter 208 forms a number of fluorescence detections by eliminating an estimate of a number of detections of Raman photons in the at least one separate time window 302, 304 on the basis of a number of detections in the Raman window 300.

For example, if the number of detections in the Raman window 300 is N and the number of detections in one fluorescence window 302 is M, the number of detections of Raman photons in the Raman window 300 may be N−k*M, where k is a coefficient which converts the number of fluorescence photons in a fluorescence window 302 to the number of fluorescence photons in the Raman window 300. If the number of detections in the Raman window 300 is 492 and the number of detections in one fluorescence window 302 is 660, the number of detections of Raman photons may be 492−k*660. The coefficient k may be 0.2, for example. Hence, the number of Raman photons in the Raman window can be estimated to be 492−0.2*660=492−132=360, where the estimate of fluorescence photons in the Raman window 300 is 132. The value of k depends on the duration of the time windows and the starting moment of the time windows, for example. The value of k may be defined on the basis of a theory, a simulation or an experiment. The above presented calculation is simple. The determination of fluorescence photons in the Raman window 300 is actually rather complicated but it may be estimated by linear or non-linear functions. The non-linear functions may be elementary functions or non-elementary functions. Correspondingly, the number of Raman photons in any fluorescence window 302, 304 may be determined on the basis of detections in the Raman window 300.

Figure 4:
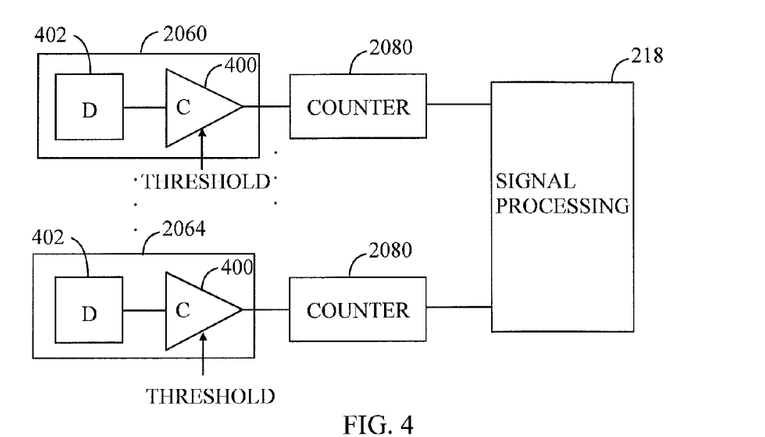
FIG. 4 illustrates an example of signal processing for determination of detections.

As to FIG. 4, each detector element 2060 to 2064 may comprise a comparator 400. In the embodiments, the comparator 400 may be integrated in the detector element 2060 to 2064 or the comparator 400 and an actual detecting element 402 may be a separate components coupled together. Each comparator 400 compares electric pulses generated by an actual detecting element 402 with a predetermined threshold. The threshold can be set to a suitable level on the basis of experiments, simulation or theory. Each counter element 2080 to 2084 then may count the number of the pulses crossing the predetermined threshold for determining the number of photons.

In an embodiment, the detector array 206 may perform detections of photons in a plurality of optical bands simultaneously. Each detector element 2060 to 2064 may detect one optical band 210, 212, 214, and at least two detector elements 2060 to 2064 detect different optical bands. The photons which are formed in response to an optical excitation pulse directed to the object 200 belong to the optical bands 210, 212, 214 measured by the detector elements 2060 to 2064 at least partly. The bandwidth of the optical bands 210 to 214 may be 1 nm to 100 nm, for instance.

In an example embodiment, the counter 208 may count a number of detections in at least two different predetermined time windows 302, 304 in at least one optical band 210, 212, 214 on the basis of the timing of the detections. One of the predetermined time windows is a Raman window 300 starting at an interaction A between the excitation pulse and the object 200. One or more separate predetermined time windows is a fluorescence window 302, 304 which starts after a beginning of the Raman window 300 in conjunction with each excitation pulse.

The counter 208 may estimate a number of fluorescence detections in the Raman window 300 on the basis of the number of detections in the at least one fluorescence window 302, 304 for each of a plurality of optical bands.

In an embodiment relating to each excitation pulse separately, the counter 208 may form a number of Raman detections in each desired optical band 210, 212, 214 by eliminating an estimate of a number of fluorescence photons in the Raman time window 300 of each of the desired optical band 210, 212, 214 on the basis of a number of detections in the at least one fluorescence window 302, 304 of each desired optical band 210, 212, 214.

In an embodiment where the counter 208 may have a clock signal available, the counter 208 may receive an electric timing mark which is based on a moment of generation of an excitation pulse from the source 216 of excitation pulses for measuring the timing of the detections with respect to the excitation pulse.

In an embodiment, the counter 208 may receive a clock signal from a separate clock circuit (not shown in Figures).

In an embodiment, the counter 208 may comprise a clock circuit (not shown in Figures) configured to provide the clock signal.

In an embodiment relating to each excitation pulse separately, the counter 208 may trigger on the timing measurement of detections at a moment of a first detection made by the detector array 206. Hence, the counter 208 may start to time the detections when the first photon from the interaction of the excitation pulse and the object 200 arrives at the detector array 206.

In an embodiment, the apparatus may comprise a controller 204 which may be coupled with the source 216 of the optical radiation. The controller 204 may form a timing signal at the moment of a generation of an electric control signal which switches the source 216 to output the optical excitation pulse, and the controller 204 may feed the timing signal as the electric timing mark to the counter 208.

In an embodiment which is shown in FIG. 5, the apparatus may comprise an optical component 500 which receives a part of each optical excitation pulse and transforms it into the electric timing mark for the counter 208. The optical component may comprise a partially transparent mirror 5000 which reflects a known part of an excitation pulse to a sensor 5002. The sensor 5002 then may output the electric timing mark in response to each excitation pulse. The electric timing mark may then be fed to the controller 204 or directly to the counter 208. FIG. 5 also shows the embodiment where the detection of photons may be performed as a transmission measurement. In the transmission measurement the excitation pulse hits the object 200 on one side and the detection is made of photons departing from the other side or from the opposite side of the object 200.

In an embodiment, the apparatus may provide the counter 208 with the electric timing mark before detections of photons of the interaction between the excitation pulse and the object 200. Alternatively in an embodiment shown in FIG. 6, the apparatus may comprise a delay circuit 600 which delays the electric timing mark by a predetermined delay. The delay circuit 600 may be before or after the controller 204. The delay circuit 600 may also be a part of the apparatus without the controller 204. The apparatus may provide the counter 208 with the electric timing mark through the delay circuit 600 after at least a first expected or realized detection. This may be useful when the counter 208 triggers the timing measurement of detections on at a moment of a first detection made by the detector array 206. The timing of a detection may be performed such that the clock starts at a detection of a photon and stops at the timing mark. Since the delay and the propagation time of the timing mark is known, the detections may be processed with their real timings with respect to the excitation. The measurement of detections may be switched off at the end of each predetermined windows 300 to 306. The switching on and off the measurement of detections can be considered as gating but now the gating is an additional feature and it doesn't control the counting since the counting is performed in the predetermined time windows 300 to 306 the periods of which may be different and independent from the gating. Instead, the gating is only a security policy to avoid noise in the measurement system.

In an embodiment, the counter 208 may measure a number of detections caused by dark current of each detector element 2060 to 2064 in a time window called a dark current window 306. During the dark current window 306 no photons from the interaction between the excitation radiation and the object 200 arrive to the detector array 206. During the dark current window 306 actually no photons ought to arrive to the detector array 206. After an excitation pulse, the dark current window 306 may start and stop before the arrival of the photons from the interaction of the very next excitation pulse and the object 200 to the detector array 206. The number of detections in the dark current window 306 may also be measured before the first excitation pulse. The length of the dark current window 306 may be 1 ps to 100 ns, for example.

In an embodiment, the counter 208 may measure a number of detections caused by dark current in the detector array 206 in a dark current window 306 which is a predetermined time window during which no photons interact with the detector elements 2060 to 2064. The counter 208 may then eliminate the number of the detections caused the dark current in the measurement of the Raman detections.

Figure 7:
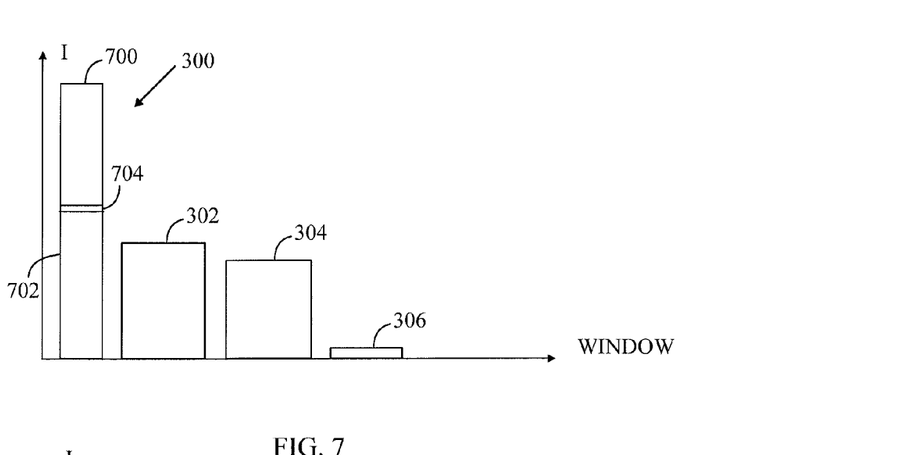
FIG. 7 illustrates an example of the number of detections in different time windows.

In an embodiment, the signal processing unit 218 may form a distribution of a number of the detections as a function of time. FIG. 7 shows detections in different time windows 300 to 306. The intensity of the optical radiation i.e. the number of detections is on vertical axis and time windows 300 to 306 are on horizontal axis. The highest part 700 of the column of the Raman window 300 illustrates the number of fluorescent detections estimated on the basis of detections in fluorescent windows 302 and 304. The middle part 704 of the column in the Raman window 300 illustrates the number of detections caused by dark current measured in the dark current window 306. The lowest part 702 illustrates detections caused by Raman radiation in Raman window 300. The number of detections may be collected from a plurality of interactions of excitation pulses since one shot of an excitation pulse doesn't necessarily always generate enough Raman and/or fluorescence photons for a good measurement. This may particularly be true for Raman photons. The distribution may be presented using a presentation means 220 which comprise a screen, for example. The presentation means 220 may also comprise a printer for presenting the distribution on paper.

Figure 8:
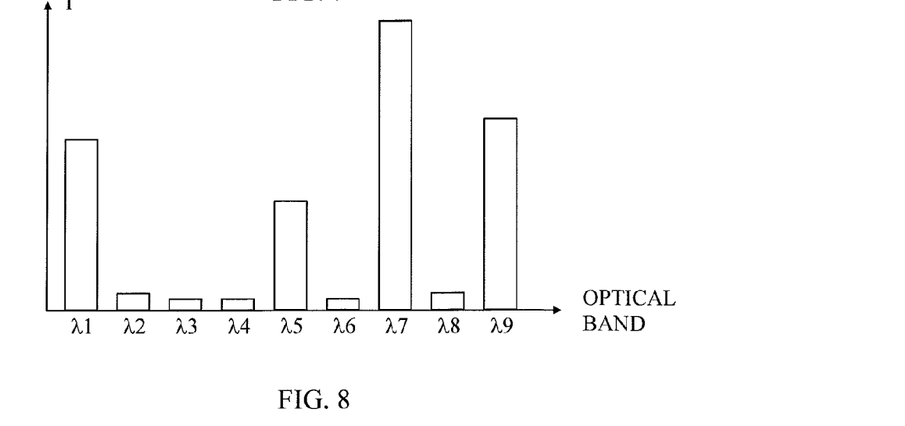
FIG. 8 illustrates an example of detections in different optical bands.

In an embodiment shown in FIG. 8, the signal processing unit 218 may form a distribution of a number of detections as a function of optical bands. It may be known on the basis of material composition that optical bands $\lambda 7$ and $\lambda 9$ refer to fluorescence of the object 200 and that optical bands $\lambda 1$ and $\lambda 5$ refer to Raman radiation of the object 200. By measuring their strength the composition of the object 200 may be determined. The rest of the optical bands are outside of the desired Raman radiation and fluorescence and thus they should have only a few detections.

In an embodiment, the counter 208 may count a number of detections in four predetermined time windows 300 to 306 on the basis of the timing of the detections (see FIG. 7). The counter 208 may count a number of detections caused by dark current in each detector element 2060 to 2064 in a dark current window 306 between periodic arrivals of photons to the detector array 206 because of the periodic interaction between the excitation pulses and the object 200. The counter 208 may count a number of detections caused by Raman and fluorescence photons in the Raman window 300. The counter 208 may count a number of detections caused by fluorescence photons in a first fluorescence window 302 separate from the dark current and the Raman windows 306, 300. Any of the one or more fluorescence windows 302, 304 and the Raman window 300 may be non-overlapping. The counter 208 may count a number of detections caused by fluorescence photons in a second fluorescence window 304. The second fluorescence window 304 may be separate from the dark current 306, the Raman and the first fluorescence windows 300, 302. The second fluorescence window 304 may be starting after the dark current, the Raman and the first fluorescence windows 306, 300, 302. The counter 208 may form a number of Raman detections by eliminating a number of the detections of the dark current on the basis of the count in dark current window 306 and eliminating an estimate of a number of fluorescence photons in the Raman time window 300, the estimate of the number of the fluorescence photons in the Raman time window 300 being based on the number of detections in the first and second fluorescence windows 302, 304.

Background noise can be limited by limiting the detections of photons to the predetermined time windows. The measurement system is electrically controlled and capable of performing measurement of Raman radiation on-line. The repetition rate is mainly limited by the detecting elements.

Figure 9:
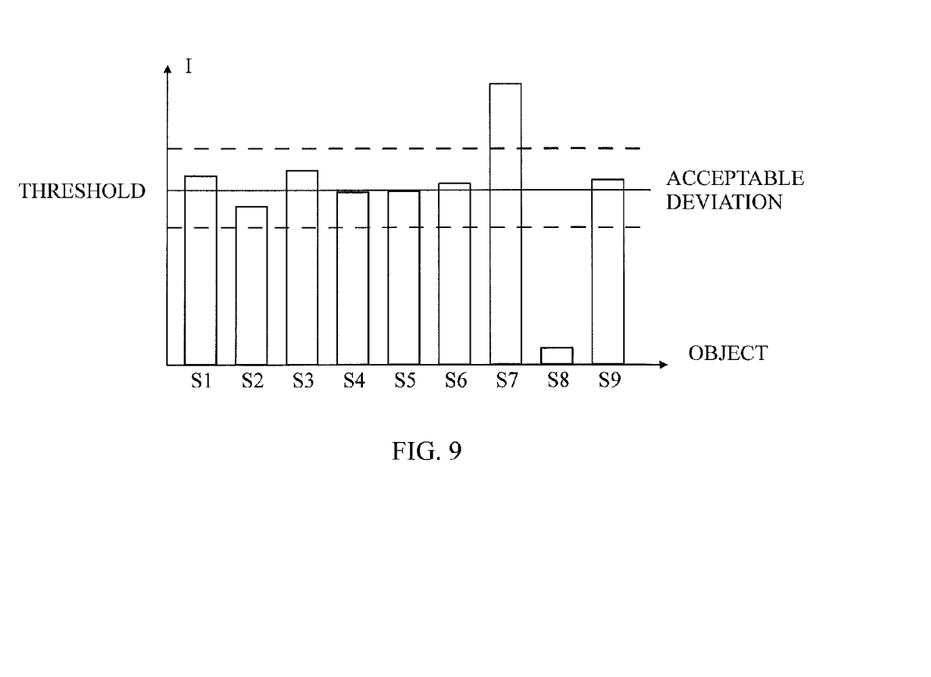
FIG. 9 illustrates an example of Raman detections in different objects.

In an embodiment shown in FIG. 9, different objects S1 to S9 have been measured. If the total number of Raman radiation or the number of detections i.e. intensity in a specified optical band is at a predetermined level, the measured object has a predetermined material composition. Otherwise the object has a wrong material composition. In FIG. 9 it can be seen that objects S1, S2, S3, S4, S5, S6 and S9 has responded properly to the excitation pulse and provided a proper number of Raman detections. However, there are far too many detection in the Raman window 300 for the object S7 and hence it has a wrong composition. The object S8 fails because it has far too few detection in the Raman window 300.

Figure 10A:
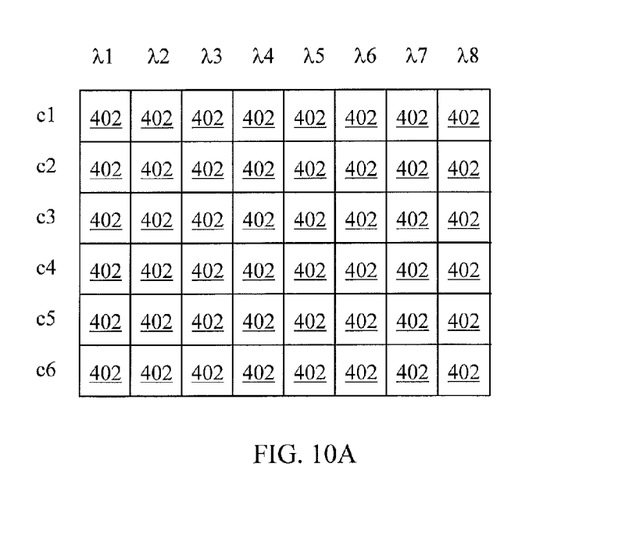
FIG. 10A illustrates an example of a matrix detector.

In an embodiment shown in FIG. 10A, the detector array 206 may comprise a matrix of detecting elements 402 where each detecting element 402 in a detector row detects a different band $\lambda 1, \lambda 2, \lambda 3, \lambda 4, \lambda 5, \lambda 6, \lambda 7$ and $\lambda 8$ of optical radiation. Each detector column c1, c2, c3, c4, c5 and c6 may detect one optical band. The detecting elements 402 may be considered as pixels. When a detector element 402 is triggered, it cannot be triggered again before a certain dead time is passed. The dead time may be around 10 ns, for example. When there are several pixels for one wavelength in different rows, two photons the temporal separation of which is less than the dead time can be detected with the matrix of pixels. A plurality of pixels also enlarges the active detection area which in turn collect more photons and increase the detection probability for a photon despite the dead time. Wavelength resolution may be made more accurate by making the pixels really smaller or relatively smaller with respect to the whole detector size which has, however, technological limits.

Figure 10B:
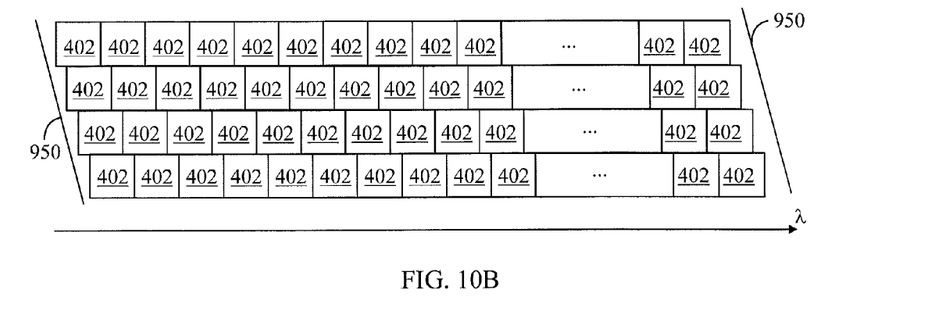
FIG. 10B illustrates an example of a matrix detector with row shifted with each other.

FIG. 10B shows a matrix detector 206 which has rows shifted with respect to each other. In an embodiment, the detector elements 402 may be arranged in any order such that a center point of a detector element 402 of a certain row is somewhere between center points of two detector elements 402 of a higher row or a lower row. FIG. 10B shows an example where rows have been shifted with each other. That is, the longitudinal axis of the slit and direction 950 of an edge of rows of the detector 206 are tilted with respect to each other. A wavelength $\lambda$ may increase in a horizontal direction from left to right as shown in FIG. 10B. Alternatively, the wavelength $\lambda$ may increase in a direction from right to left.

Figure 10C:
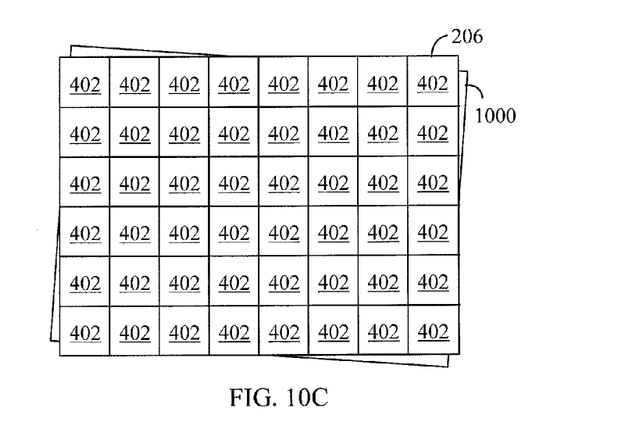
FIG. 10C illustrates an example of a skewed matrix detector.

FIG. 10C shows a matrix detector 206 which is skewed with respect to the exit aperture 1000 of the spectrometer. It may also be considered that the exit aperture 1000 of the spectrometer is skewed with respect to the matrix detector 206. That is, the longitudinal axis of the slit is tilted with respect to the axis of a row of the detector 206. Wavelength may increase in a horizontal direction from left to right as shown in FIG. 10C. Alternatively, the wavelength may increase in a direction from right to left.

By having the rows of the matrix detector 206 shifted or skewed it is possible to improve the wavelength resolution for the detected photons even without changes in real or relative pixel sizes.

If a detecting element 402 doesn't operate properly, it may be deleted by an impact of a laser pulse, for example. Failure in operation may mean the dark count rate is much higher than with other elements on average, for example. Still, other detecting elements operate properly and the measurement may continue. The matrix may also be covered by a mask so that the improperly operating element cannot receive photons. Still, the improperly operating element may be electrically gated such that it doesn't receive operating voltage during the time windows 300 to 306 when the detections are made. The operating voltage may completely be cut for the detecting element which is out of order.

The optical pulse which is received from the object 200 may be scanned over the matrix in order to avoid too heavy bombardment of photons to the detecting elements 402.

The controller 204 may be a rather simple electronic circuit particularly in the case when the measuring state of the detecting elements is triggered on and off synchronously with the excitation optical pulses of the optical radiation source 216. However, the controller 204 and the signal processing unit 118 may also be implemented as an electronic digital computer, which may comprise a working memory (RAM), a central processing unit (CPU), and a system clock. The CPU may comprise a set of registers, an arithmetic logic unit, and a control unit. The program instructions may be coded by a programming language.

The computer program or programs, which is used for controlling the detecting elements 2060 to 2064 and the optical radiation source 216 and performing the signal processing, may be stored in some sort of carrier, which may be any entity or device capable of carrying the program.

Next, a method will be described with reference to FIG. 11. In step 1100, performing, by a detector, detections of photons of optical radiation formed in an interaction between an optical excitation pulse and the object. In step 1102, measuring, in a counter, timing of each detection made in the detector array with respect to the excitation pulse causing the detected photons, and performing at least one of the following: forming a number of Raman detections, forming a number of fluorescence detections. In step 1104, forming the number of the Raman detections being performed by eliminating an estimate of a number of fluorescence photons in the measurement, the estimate being formed in a predetermined manner from the number and timing of the detections, or forming the number of the fluorescence detections being performed by eliminating an estimate of a number of Raman photons in the measurement, the estimate being formed in a predetermined manner from the number and timing of the detections.

The apparatus and the method may be applied in various processes, which may be performed in a medical and paper industry, for example. An effective molecule and/or its presence may be determined and its concentration in the medium may also be determined.

Counting detections of fluorescence and Raman radiation only in time windows 300 to 306 associated with each excitation pulse filters the background noise out effectively, since outside the predetermined time windows 300 to 306 no detections are counted. In addition to background noise either photons of fluorescence or Raman radiation may be filtered out in a desired time window by an estimation of unwanted photons in the desired time window on the basis of detections in one or more separate windows.

The apparatus is suitable for field experiments and on-line measurements due to at least one of the following: low background noise, fluorescence suppression, simplicity, small size, reliability and low cost. That counting of detections may be performed independent from gating makes the counting of detections flexible and it may be adapted in a programmable manner case by case. Hence, the adaptation may be made during analyzing the measurements instead of or in addition to a change in gating during the measurement. The counting of each detection allows more measurement data in a shorter period of time.

Figure 11:
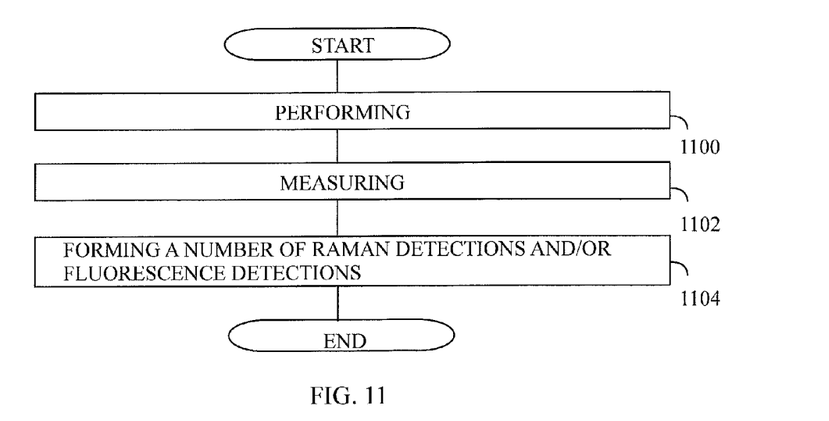
FIG. 11 shows an example of a flow chart of the method.

The measuring units 206, 208, 216 and the controller 204 capable of performing the steps presented in at least one of FIG. 11 may be implemented as an electronic digital computer, or a circuitry which may comprise a working memory (RAM), a central processing unit (CPU), and a system clock. The CPU may comprise a set of registers, an arithmetic logic unit, and a controller. The controller or the circuitry is controlled by a sequence of program instructions transferred to the CPU from the RAM. The controller may contain a number of microinstructions for basic operations. The implementation of microinstructions may vary depending on the CPU design. The program instructions may be coded by a programming language, which may be a high-level programming language, such as C, Java, etc., or a low-level programming language, such as a machine language, or an assembler. The electronic digital computer may also have an operating system, which may provide system services to a computer program written with the program instructions.

The measuring units 206, 208, 216 and the controller 204 may comprise circuitries which refer to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present.

As a further example, the term 'circuitry' would also cover an implementation of merely a processor (or multiple processors) or a portion of a processor and its (or their) accompanying software and/or firmware.

An embodiment provides a computer program embodied on a distribution medium, comprising program instructions which, when loaded into an electronic apparatus, are configured to control the apparatus to execute the embodiments described above.

The computer program may be in source code form, object code form, or in some intermediate form, and it may be stored in some sort of carrier, which may be any entity or device capable of carrying the program. Such carriers include electrical carrier signal, telecommunications signal, a record medium, computer memory, read-only memory, and a software distribution package, for example. Depending on the processing power needed, the computer program may be executed in a single electronic digital computer or it may be distributed amongst a number of computers.

The apparatus, particularly the detector 206 and the counter 208, may be implemented as one or more integrated circuits, such as application-specific integrated circuits ASIC (Application Specific Integrated Circuit). Other hardware embodiments are also feasible, such as a circuit built of separate components. A hybrid of different implementations may also be feasible. The circuits of the detector 206 and the counter 208 may at least partly be based on CMOS (Complementary Metal Oxide Semiconductor) technology. When selecting the method of implementation, a person skilled in the art will consider the requirements set for the size and power consumption of the apparatus, the necessary processing capacity, production costs, and production volumes, for example.

It will be obvious to a person skilled in the art that, as technology advances, the inventive concept can be implemented in various ways. The invention and its embodiments are not limited to the examples described above but may vary within the scope of the claims.

The invention claimed is:

1. An apparatus for measuring inelastic scattering from an object comprises: a semiconductor single-photon avalanche detector, and a counter;
    the detector being configured to perform detections of single photons of optical radiation formed in an interaction between an optical excitation pulse and the object;
    the counter being configured to
    measure timing of each detection made in the detector with respect to the excitation pulse causing the detected photons,
    perform at least one of the following: forming a number of Raman detections in a Raman time window, forming a number of fluorescence detections in at least one fluorescence time window, the beginning moment of the at least one fluorescence window being after the beginning of the Raman window, where
    the counter is, related to the Raman detections, configured to form the number of the Raman detections by eliminating an estimate of a number of fluorescence photons in the Raman window, the estimate being formed on the basis of a number of the detections in the at least one fluorescence window, or
    the counter is, related to the fluorescence detections, configured to
    form the number of the fluorescence detections by eliminating an estimate of a number of Raman photons in the at least one fluorescence window, the estimate being formed on the basis of a number of the detections in the Raman window.

2. The apparatus of claim 1, wherein the counter being configured to
    measure timing of each detection made in the detector with respect to the excitation pulse causing the detected photons,
    count a number of detections in at least two different predetermined time windows on the basis of the timing of each detection, one of the predetermined time windows being a Raman window starting at an arrival of the optical radiation from the interaction between the optical excitation pulse and the object and at least one separate time window each of which being a fluorescence window starting after a beginning of the Raman window, and
    perform at least one of the following: form a number of Raman detections by eliminating an estimate of a number of fluorescence photons in the Raman time window on the basis of a number of detections in the at least one fluorescence window, form a number of fluorescence detections by eliminating an estimate of a number of Raman photons in the at least one separate time window on the basis of a number of detections in the Raman window.

3. The apparatus of claim 1, wherein the detector comprises a detector array with a plurality of detector elements, the detector being configured to perform detections of photons in a plurality of optical bands simultaneously such that each detector element is configured to detect one optical band, the photons which are formed in response to an optical excitation pulse directed to the object belonging to the optical bands;
the counter being configured to
count a number of detections in at least one optical band on the basis of the timing of each detection, and
perform at least one of the following: form a number of Raman detections by eliminating an estimate of a number of detections of fluorescence photons in the Raman time window of each of the desired optical band on the basis of a number of detections in the at least one fluorescence window of each of the desired optical band, form a number of fluorescence detections by eliminating an estimate of a number of detections of fluorescence photons in the at least one separate time window of each of the desired optical band on the basis of a number of detections in the Raman window of each of the desired optical band.

4. The apparatus of claim 3, wherein the signal processing unit is configured to form a distribution of a number of detections as a function of optical bands.

5. The apparatus of claim 1, wherein the counter has a clock signal available, and the counter is configured to receive an electric timing mark based on a moment of generation of the excitation pulse from the source of excitation pulses for measuring the timing of each detection with respect to the excitation pulse.

6. The apparatus of claim 5, wherein the apparatus comprises a delay circuit configured to delay the electric timing mark by a predetermined delay, and the apparatus is configured to provide the counter with the electric timing mark through the delay circuit after at least a first expected detection.

7. The apparatus of claim 5, wherein the counter is configured to receive a clock signal from a separate clock circuit.

8. The apparatus of claim 5, wherein the counter comprises a clock circuit configured to provide the clock signal.

9. The apparatus of claim 1, wherein the counter is configured to switch on the time measurement of detections at the first detection.

10. The apparatus of claim 5, wherein the apparatus is configured to provide the counter with the electric timing mark before detections.

11. The apparatus of claim 5, wherein the apparatus comprising a controller couplable with the source of the excitation pulse, the controller being configured to form a timing signal at a moment of the electric control signal switching the source of the excitation pulse to output the optical excitation pulse, the timing signal acting as the electric timing mark.

12. The apparatus of claim 5, wherein the apparatus comprises an optical component configured to receive a part of the optical excitation pulse and to transform it into the electric timing mark for the counter.

13. The apparatus of claim 1, wherein the apparatus comprises a signal processing unit configured to form a distribution of a number of the detections as a function of time.

14. The apparatus of claim 1, wherein the counter is configured to measure a number of detections caused by dark current of the detector in a dark current window which is a time window without photons from the interaction of the excitation pulse and the object to the detector; and
the counter is configured to eliminate a number of the detections caused the dark current from at least one of the following: the number of the Raman detections, the number of the fluorescent detections.

15. The apparatus of claim 14, wherein the counter is configured to count a number of detections in at least four predetermined time windows on the basis of the timing of each detection,
the counter is configured to count a number of detections caused by
dark current of each detector element in the dark current window,
Raman and fluorescence photons in the Raman window,
fluorescence photons in a first fluorescence window, and
fluorescence photons in a second fluorescence window separate from the dark current window and starting after the Raman and the first fluorescence time window; and
the counter is configured to form a number of Raman and fluorescence detections by eliminating a number of the detections caused by the dark current on the basis of the count in dark current window for forming at least one of the following: the number of Raman detections, the number of fluorescence detections, the estimate of the number of the fluorescence photons in the Raman time window being based on the number of detections in the first and second fluorescence windows.

16. The apparatus of claim 1, wherein the detector has rows shifted with respect to each other.

17. The apparatus of claim 1, wherein rows of the detector and an exit aperture of a spectrometer are skewed with respect to each other.

18. A method for measuring inelastic scattering from an object, the method comprising:
performing, by a detector, detections of single photons of optical radiation formed in an interaction between an optical excitation pulse and the object;
measuring, in a counter, timing of each detection made in the detector array with respect to the excitation pulse causing the detected photons, and performing at least one of the following:
forming a number of Raman detections in a Raman time window, forming a number of fluorescence detections in at least one fluorescence time window, the beginning moment of the at least one fluorescence window being after the beginning of the Raman window, where
related to the Raman detections
forming the number of the Raman detections by eliminating an estimate of a number of fluorescence photons in the Raman window, the estimate being formed on the basis of the number of the detections in the at least one fluorescence window, or
related to the fluorescence detections
forming the number of the fluorescence detections by eliminating an estimate of a number of Raman photons in the at least one fluorescence window, the estimate being formed on the basis of the number of the detections in the Raman window.

19. The method of claim 18, the method further comprising counting, in the counter, a number of detections in at least two different predetermined time windows on the basis of the timing of each detection, one of the predetermined time windows being a Raman window starting at an arrival of the optical radiation from the interaction between the optical excitation pulse and the object and at least one separate time window each of which being a fluorescence window starting after a beginning of the Raman window, and
performing, in the counter, at least one of the following: forming a number of Raman detections by eliminating an estimate of a number of detections of fluorescence photons in the Raman time window on the basis of a number of detections in the at least one fluorescence window, forming a number of fluorescence detections by eliminating an estimate of a number of detections of Raman photons in the at least separate time window on the basis of a number of detections in the Raman window.

20. The method of claim 18, the method further comprising performing, by a detector array, detections of photons in a plurality of optical bands simultaneously such that each detector element detects one optical band, the photons formed in response to an optical excitation pulse directed to the object belonging to the optical bands;

counting a number of detections in at least one optical band on the basis of the timing of each detection, and performing at least one of the following: forming a number of Raman detections in each desired optical band by eliminating an estimate of a number of detections of fluorescence photons in the Raman time window of each of the desired optical band on the basis of a number of detections in the at least one fluorescence window of each of the desired optical band, forming a number of fluorescence detections in each desired optical band by eliminating an estimate of a number of detections of Raman photons in the at least one fluorescence time window of each of the desired optical band on the basis of a number of detections in the Raman window of each of the desired optical band.

21. The method of claim 18, the method further comprising measuring, by the counter, a number of detections caused by dark current of the detector in a dark current window which is a time window without the photons from the interaction between the excitation pulse and the object to the detector, and eliminating, in the counter, a number of the detections caused the dark current from at least one of the following: the number of the Raman detections, the number of the fluorescence detections.

22. An apparatus measuring inelastic scattering from an object, the apparatus comprising:

at least one processor; and at least one memory including a computer program code, wherein the at least one memory and the computer program code are configured, with the at least one processor, to cause the apparatus at least to perform:

detecting, by the detector, single photons of optical radiation formed in an interaction between an optical excitation pulse and the object;

measuring, in a counter, timing of each detection made in the detector array with respect to the excitation pulse causing the detected photons, and performing, in a counter, at least one of the following: forming a number of Raman detections in a Raman time window, forming a number of fluorescence detections in at least one fluorescence time window, the beginning moment of the at least one fluorescence window being after the beginning of the Raman window, where related to the Raman detections forming the number of the Raman detections by eliminating an estimate of a number of fluorescence photons in the Raman window, the estimate being formed on the basis of the number of the detections in the at least one fluorescence window, or related to the fluorescence detections forming the number of the fluorescence detections by eliminating an estimate of a number of Raman photons in the at least one fluorescence window, the estimate being formed on the basis of the number of the detections in the Raman window.

23. The apparatus of claim 22, wherein counting a number of detections in at least two different predetermined time windows on the basis of the timing of each detection, one of the predetermined time windows being a Raman window starting at an arrival of the optical radiation from the interaction between the optical excitation pulse and the object and at least one separate time window each of which being a fluorescence window starting after a beginning of the Raman window, and performing, in the counter, at least one of the following: forming a number of Raman detections by eliminating an estimate of a number of detections of fluorescence photons in the Raman time window on the basis of a number of detections in the at least one fluorescence window, forming a number of fluorescence detections by eliminating an estimate of a number of detections of Raman photons in the at least one separate time window on the basis of a number of detections in the Raman window.

* * * * *